United States Patent [19]

Mitsuda et al.

[11] Patent Number: 4,985,365
[45] Date of Patent: Jan. 15, 1991

[54] PROCESS FOR PRODUCING OPTICALLY ACTIVE BENZYL ALCOHOL COMPOUND

[75] Inventors: Satoshi Mitsuda, Osaka; Noritada Matsuo, Hyogo; Hideo Hirohara, Osaka, all of Japan

[73] Assignee: Sumitomo Chemical Company, Ltd., Osaka, Japan

[21] Appl. No.: 201,927

[22] Filed: Jun. 3, 1988

Related U.S. Application Data

[63] Continuation-in-part of Ser. No. 668,373, Oct. 1, 1984, abandoned, and a continuation-in-part of Ser. No. 443,756, Nov. 22, 1982, abandoned, and a continuation-in-part of Ser. No. 567,342, Dec. 30, 1983, abandoned.

[30] Foreign Application Priority Data

| Nov. 28, 1981 | [JP] | Japan | 56-191340 |
| Jun. 2, 1982 | [JP] | Japan | 57-95207 |
| Jan. 10, 1983 | [JP] | Japan | 58-002602 |
| Jan. 10, 1983 | [JP] | Japan | 58-002604 |
| Jan. 10, 1983 | [JP] | Japan | 58-002603 |
| May 9, 1983 | [JP] | Japan | 58-081442 |

[51] Int. Cl.$^5$ .............................................. C12P 7/02
[52] U.S. Cl. ................................. 435/280; 435/155; 435/156; 435/253.3; 435/254; 435/255; 435/822
[58] Field of Search ..................... 435/280, 155, 156

[56] References Cited

U.S. PATENT DOCUMENTS

| 3,652,395 | 12/1966 | Nakao et al. |
| 3,669,836 | 4/1967 | Nakao et al. |
| 3,733,253 | 1/1973 | Suzuki et al. |
| 3,871,957 | 5/1973 | Mohan et al. |
| 4,283,494 | 6/1981 | Kokushio et al. |
| 4,897,357 | 1/1990 | Smith et al. ............... 435/280 |

FOREIGN PATENT DOCUMENTS

| 2447899 | 8/1980 | France. |
| 49-32080 | 7/1974 | Japan. |
| 56-48888 | 5/1981 | Japan. |
| 1275180 | 5/1972 | United Kingdom. |
| 2097373 | 11/1982 | United Kingdom. |

OTHER PUBLICATIONS

Wlodarczyk et al., Effect of Sodium Salts of Benzoic Acid and Sorbic Acids on *Bacillus Cerus* and *Torulpsis Candida*, 35 *Roczn. Pzh.* 557 (1984).
*CRC Handbook of Microbiology*, vol. 1, 248–258 (2nd ed. 1977).
Singleton et al., *Dictionary of Microbiology* 719–720 (1987).
McGraw et al., *World Directory of Collections of Cultures of Microrganisms*, XXVI, 252–253, 289 (1982).
*ATCC Catalogue of Fungi/Yeasts*, 17th Edition, 73, 182–183 (1987).
*ATCC Update Bacteria/Phages* 1 (Mar. 1986).
*ATCC Catalogue of Strains I*, 15th Edition, 517 (1982).
*List of Cultures* (Institute for Fermentation) 7th Edition, 13, 28, 29, 41, 90 (1984).
*List of Cultures* (Institute for Fermentation) Supp. to 5th Edition, 50 (1975).
Schlemmer et al., Purification and Characterization of a Pectin Lyase Produced by *Pseudomonas Fluorescens* W51, 169 *J. Bacteriology* 4493 (1987).
Yamaguichi et al., Production and Properties of Lipase from a Newly Isolated *Chromobacterium*, 37, *Agr. Biol. Chem.* 999 (1973).
St. Germain et al. Torulopsis Candida, A New Opportunistic Pathogen, 24, *J. Clinical Microbiology* 884 (1986).
Tanaka et al., Intermolecular Fructosyl and Levanbiosyl Transfers by Levan Fructotransferase of *Arthrobactor Ureafaciens*, 97, *J. Biochem.* 1679 (1985).
Catalogue of Bacteria Phages rDNA Vectors, pp. 3, 16 151,209 (ATCC 1985).
Ohta et al., Asymmetric Hydrolysis of Aryloxyacetaldehyde Cyanohydrin Acetates, 50 Agric. Biol. Chem. 3181 (1986).
Matsuo et al., Preparation of Optically Active 1-Acetoxy-2-Aryl-Oxypropionitriles and Application to a Facile Synthesis of (S)-(−)-Propanolol, 45 Tetrahedron Letters 5533–5534 (1985).
Sugai et al., Preparation of Optically Active Secondary Alcohols Related to Synthetic Pyrethroids by Microbial Asymmetric Hydrolysis of the Corresponding Acetates, 45 Agric. Biol. Chem. 2579 (1982).
Enzymes in Organic Synthesis, p. 128, (1985).

*Primary Examiner*—Sam Rosen
*Attorney, Agent, or Firm*—Cushman, Darby & Cushman

[57] ABSTRACT

A process for preparing resolved (S)-(−)-α-cyano-3-phenoxybenzyl alcohol or an (S)-isomer-rich optically active α-cyano-3-phenoxybenzyl alcohol compound.

22 Claims, No Drawings

PROCESS FOR PRODUCING OPTICALLY ACTIVE BENZYL ALCOHOL COMPOUND

RELATED APPLICATIONS

This application is a continuation-in-part of U.S. application Ser. No. 06/668,373 filed Oct. 1, 1984; and also a continuation-in-part of U.S. application Ser. No. 06/443,756 filed Nov. 22, 1982 and U.S. application Ser. No. 06/567,342 filed Dec. 30, 1983, all now abandoned, and the disclosures of which are incorporated herein by reference.

FIELD OF THE INVENTION

Processes for producing optically active α-cyano-3-phenoxy benzyl alcohol compounds and certain derivatives thereof are disclosed herein.

BACKGROUND OF THE INVENTION

α-cyano-3-phenoxy benzyl alcohol compounds have been known as the novel alcoholic moiety of a series of synthetic pyrethroid ester compounds which exhibit excellent insecticidal activity. Synthetic pyrethroid esters such as, for example, fenvalerate, cypermethrin, deltamethrin, have an α-cyano-3-phenoxy benzyl alcohol moiety and are good insecticides for household and sanitary uses as well as agricultural use, since such synthetic pyrethroid esters possess sufficient photostability combined with significant insecticidal activity.

Since the α-cyano-benzyl alcohol compound has an asymmetric carbon at the α-position thereof, there are two optical isomers. With respect to insecticidal activity as an ester, the (S)-isomer ester of the α-cyano-benzyl alcohol compound is much superior to the antipode (R)-isomer ester. (See Hirosuke Yoshioka, Fournal of Synthetic Organic Chemistry, Japan, vol. 38, No. 12, pp. 1151–1162 (1980)). Accordingly, the development of commercially useful technology has been desired in order to optically resolve the (R,S)-isomer of said α-cyano-benzyl alcohol compound to obtain the (S)-isomer thereof and particularly the resolved (or at least substantially resolved) (S)-α-cyano-3-phenoxy benzyl alcohol.

However, since the α-cyano-benzyl alcohol compound is unstable, the optical resolution thereof is not easy. Methods now available for the optical resolution of this alcohol are complicated and require expensive optically active agents.

The conventional optical resolution process for alcohols is effected via an ester or a half-ester with an ordinary optically active organic acid may not be advantageous for use in resolving the (R,S)-isomer of the α-cyano-3-phenoxy benzyl alcohol compound. Methods for obtaining (S)-α-cyano-3-phenoxybenzyl alcohol include the following: (1) a method wherein the desired (S)-α-cyano-3-phenoxybenzyl alcohol is obtained by reacting (R,S)-α-cyano-3-phenoxybenzyl alcohol with cis-2,2-dimethyl-3(S)-(dihydroxy-methyl)-cyclopropane-1(R)carboxylic acid lactone in the presence of an acidic reagent to obtain an ether compound, separating each isomer from the resulting mixture of two kinds of the isomers using physical separation techniques, and hydrolyzing the ether compound containing (S)-isomer alcohol component in an acidic medium (see Japanese Unexamined Published Patent Application No. 109944/1979); and (2) a method wherein (S)-α-cyano-3-phenoxybenzyl alcohol is obtained by reacting an (S)-α-cyano-3-phenoxybenzyl alcohol ester of a chiral cyclopropane-carboxylic acid with a boron halide and then with water (see Japanese Unexamined Published Patent Application No. 12355/1981). However, these methods are complicated and require an expensive optically active reagent. The overall yields are also not particularly high. Furthermore, in method (2), the optically active α-cyano-3-phenoxybenzyl alcohol ester has to be prepared in advance. Based on these points, the methods heretofore known can not necessarily be said to be satisfactory.

SUMMARY OF THE PRESENT INVENTION

Development of a commercially advantageous process for producing an (S)-isomer rich and/or the resolved (S)-α-cyano-benzyl alcohol compound has long been desired. It has now been found that biochemically asymmetric hydrolysis of a racemic isomer, namely, an (R,S)-isomer of the ester of the α-cyano-benzyl alcohol compound as the starting material, efficiently resolves the ester into the (S)-isomer or (S)-isomer-rich optically active α-cyano-benzyl alcohol compound and the antipode ester thereof as more fully described herein below. The antipode ester can then be separated.

DETAILED DESCRIPTION OF THE INVENTION

A method for preparing (S)-α-cyano-3-phenoxybenzyl alcohol is now disclosed wherein an organic carboxylic acid (saturated or unsaturated, having 1 to 18 carbon atoms) ester of (R,S)-α-cyano-3-phenoxybenzyl alcohol is subjected to asymmetric hydrolysis using an esterase originated from a microorganism or an animal pancreas or liver, which enzyme is capable of asymmetrically hydrolyzing the ester of the (S)-α-cyano-3-phenoxybenzyl alcohol predominantly, at not higher than pH 7 to asymmetrically hydrolyze the ester, whereby the (S)-α-cyano-3-phenoxybenzyl alcohol and the ester of its antipode are obtained.

The (S)-isomer-rich (and/or the (S)-isomer) optically active α-cyano-benzyl alcohol compound represented by the formula (II) is obtained:

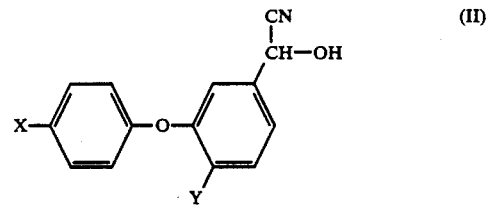

wherein Y is a fluorine atom or hydrogen atom, X is a hydrogen atom, a flourine atom, a chlorine atom or a bromine atom, which process comprises allowing an esterase originating from microorganisms or an animal pancreas or liver to react at not higher than pH 7 with an ester of (R,S)-α-cyano-benzyl alcohol represented by the Formula (I):

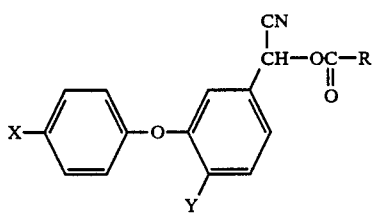

$$\text{(I)}$$

wherein X and Y have the same meaning as above; (A) R means the residue of a saturated or unsaturated $C_1$-$C_{18}$ organic carboxylic acid when both X and Y are hydorogen; (B) when Y is a fluorine then R means a hydrogen atom, a $C_1$-$C_{18}$ alkyl, $C_2$-$C_{18}$ alkenyl, $C_2$-$C_{18}$ alkynyl, $C_1$-$C_4$ halogen-substituted alkyl, $C_2$-$C_4$ halogen-substituted alkenyl, $C_2$-$C_4$ -halogen-substituted alkynyl, $C_1$-$C_8$ alkoxyl, $C_2$-$C_8$ -alkenyloxy or $C_2$-$C_8$ alkynyloxy group; or (C) when X and Y are hydrogen, R may mean a $C_1$-$C_8$ alkoxyl group, $C_1$-$C_8$-alkenyloxy, $C_1$-$C_8$ alkynyloxy, $C_1$-$C_4$ halogen-substitute alkyl, $C_1$-$C_4$ halogen-substituted alkenyl, $C_1$-$C_4$ halogen-substituted alkynyl, carboxyl, $C_2$-$C_4$ hydroxycarbonyalkyl which may be substituted with lower alkyl or halogen, or $C_3$-$C_4$ hydroxycarbonylalkynyl which may be substituted with lower alkyl or halogen, in order to asymmetrically hydrolyze the same until it is resolved into an (S)-isomer-rich α-cyano-benzyl alcohol compound represented by the Formula (II) and an antipode ester thereof, the esterase being able to act upon the ester of (R,S)-isomer of the α-cyano-benzyl alcohol compound represented by the Formula (I) and to predominantly perform asymmetric hydrolysis to the desired (S)-isomer of the ester of the α-cyano-benzyl alcohol compound.

The term "esterase" as used herein has a broad meaning including a lipase having activity to a water-insoluble substrate. The esterases employable in the present invention are those capable of asymmetrically hydrolyzing the (S)-isomer ester(or the ester of the (S)-α-cyano-3-phenoxybenzyl alcohol) predominantly and they originate from microorganisms and from animal pancreases or livers.

Any microorganism which produces the esterase used in the present invention can be employed, no matter what genus and species the microorganism belongs to, as long as the microorganism produces the esterase which is capable of asymmetrically hydrolyzing (R,S)-isomer of the ester represented by the Formula (I) and to predominantly obtain the ester of (S)-isomer of the ester of alcohol compound or predominately the resolved (S)-isomer of the alcohol compound.

When X and Y in Formula I are hydrogen and R is the residue of an organic carboxylic and (saturated or unsaturated, having 1-18 carbon atoms), exemplary genuses of microorganisms for use in the method for preparing (S)-α-cyano-3-phenoxybenzyl alcohol are as follows: Arthrobacter, Alcaliqenes, Achromobacter, Pseudomonas, Aspergillus, Mucor, Chromobacterium, Bacillus, Micrococcus, Candida, Torulopsis, Nocardia, Rhodotorula, Brevibacterium, Enterobacter, Flavobacterium, Mycobacterium, Corynebacterium, Lactobacillus, Streptomyces, Trichoderma, Penicillium, Rhizopus, Aureobasidium, Actinomucor, Gibberella, Geotricum, Absidia, Cunninghamella, Gliocladium, Saccharomyces, Cryptococcus, Pichia, or Hansenula. The esterase originating from the microoganisms belonging to the following genuses is preferred from the viewpoints of optical selectivity and hydrolysis capability: Arthrobacter, Alcaliqenes, Achromobacter, Pseudomonas, Aspergillus, Chromobacterium, Candida, Torulopsis, Nocardia, Rhodotorula, Brevibacterium, Mycobacterium, Streptomyces, Trichoderma, Rhizopus or Geotrium.

Such microorganisms may be cultured in a liquid medium according to the conventional procedure. For example, a microorganism may be inoculated to a sterilized liquid medium (e.g., a bouillon medium for bacteria, a malt extract - yeast extract medium for fungi and yeasts), and subjected to a shaken culture ordinarily at a temperature of 20° to 40° C. for 2 to 3 days. If necessary, it may be cultured on a solid medium.

In the ester of the Formula I, when X and Y are hydrogen and when R is an alkoxyl group having 1 to 8 carbon atoms, an alkenyloxy group having 1 to 8 carbon atoms or an alkynyloxy group having 1 to 8 carbon atoms, then the employable esterases are the esterases originating from these genuses: Arthrobacter, Achromobacter, Pseudomonas, Chrombacterium, Bacillus, Brevibacterium, Nocardia, Rhodotorula, Candida, Trichoderma, Rhizopus, Mucor, Aspergillus, Geotricum, Aureobasidium, Hansenula, Torulopsis and Alcaligenes. Further, when X and Y are hydrogen and the ester of Formula I is the ester of a halogen substituted organic carboxylic acid, i.e., when R is a $C_1$-$C_4$ halogen-substituted alkyl group, a $C_1$-$C_4$, alkenyl group or a $C_1$-$C_4$ halogen-substituted alkynyl group, the employable esterases are the esterases originated from an animal pancreas, an animal liver, or microorganisms of the genuses listed below: Arthrobacter, Pseudomonas, Chromobacterium, Bacillus, Candida, Nocardia, Rhodotorula, Brevibacterium, Trichoderma, Rhizopus, Mucor, Aspergillus, Geotricum, Hansenula, Enterobacter, Flavobacterium, Mycobacterium, Corynebacterium, Lactobacillus, Streptymices, Penicillium, Actinomucor, Gibberella, Absidia, Cunninghamella, Gliocladium, Sacharomyces, Cryptococcus, Pichia, Micrococcus, Torulopsis, Aureobasidium, Alcaligenes and Achromobacter. In particular from the viewpoints of optical selectivity and hydrolyzing ability, enzymes obtained from the microorganisms belonging to genuses: Arthrobacter, Archromobacter, Pseudomonas, Chromobacterium, Bacillus, Brevibacterium, Nocardia, Rhodotorula, Candida, Trichoderma, Rhizopus, Mucor, Aspergillus, Geotricum, Aureobasidium, Hansenula and Torulopsis, are preferred.

When X and Y are hydrogen and the ester of Formula I is a half-ester, i.e., when R is a carboxyl group, a hydroxycarbonylalkyl group having 2 to 4 carbon atoms which may be substituted with lower alkyl group or halogen atom, a hydroxycarbonyl alkenyl group having 3 to 4 carbon atoms which may be substituted with lower alkyl group or halogen atom, or a hydroxycarbonyl alkynyl group having 3 to 4 carbon atoms which may be substituted with lower alkyl group or halogen atom, the employable esterases are the esterases originated from microorganisms of the genuses ilustrated below: Arthrobacter, Chromobacterium, Rhodotolura, Torulopsis, Hansenula and Candida.

When Y in Formula I is a fluorine atom and X is a hydrogen atom, chlorine atom, bromine atom or fluorine atom, esterases originating from microorganisms such as those belonging to genuses Arthrobacter, Alcaligenes, Achromobacter, Pseudomonas, Chromobacterium, Bacillus, Brevibacterium, Nocardia, Rhodotorula, Candida, Trichoderma, Rhizopus, Mucor, Aspergillus, Geotricum, Aureobasidium, Hansenula, and Torulopsis are suitable. From the viewpoints of hydrolysis capability and optical purity of the optically active α-cyanobenzyl alcohol compound represented by the Formula (II) when X is H, Cl, Br or F and Y is F, an esterase produced by microorganisms belonging to genuses Arthrobacter, Alcaligenes, Achromobacter, Pseudomonas and Chromobacterium is preferred.

As the typical examples of microorganisms belonging to those genuses mentioned above, there can be illustrated following strains.

| (1) | Arthrobacter simplex | IFO-3530 |
|---|---|---|
| (2) | Alcaligenes faecalis | IFO-12669 |
| (3) | Achromobacter sp. | ATCC-21910 |
| (4) | Pseudmonas fluorescens | IFO-3081 |
| (5) | Chromobacterium viscosum | ATCC-6918 |
| (6) | Bacillus licheniformis | IFO-12197 |
| (7) | Brevibacterium anmoniagenes | IFO-12072 |
| (8) | Nocardia erythropolis | IFO-12320 |
| (9) | Rhodotorula minuta var. texensis | IFO-0879 |
| (10) | Candida utilis | IFO-1086 |
| (11) | Trichoderma viride | IFO-4847 |
| (12) | Rhizopus chinensis | IFO-4737 |
| (13) | Mucor javanicus | IFO-4572 |
| (14) | Aspergillus var. asper | IFO-5324 |
| (15) | Geotricum candidum | IFO-5368 |
| (16) | Aureobasidium pullulans | IFO-4464 |
| (17) | Hansenula anomala | IFO-0707 |
| (18) | Torulopsis candida | IFO-0380 |

In Formula I when X and Y are both hydrogen and R is the residue of an organic carboxylic acid (saturated or unsaturated), microorganisms such as (5), (6), (7), (8), (10), (11), (15), (16), (17) and (18) listed by numbers hereinabove as well as the following may be employed.

| (19) | Micrococcus luteus | IFO-3066 |
|---|---|---|
| (20) | Rhodotorula minuta | IFO-0387 |
| (21) | Enterobacter cloacae | IFO-3320 |
| (22) | Flavobacterium arborescens | IFO-3750 |
| (23) | Mycobacterium phlei | IFO-3185 |
| (24) | Corynebacterium equi | ATCC-7699 |
| (25) | Pichia polimorpha | IFO-1166 |
| (26) | Cryptococcus albidus | IFO-0378 |
| (27) | Lactobacillus casei | IFO-3322 |
| (28) | Saccharomyces ruoxii | IFO-0505 |
| (29) | Penicillium frequentans | IFO-5692 |
| (30) | Actinomucor elegans | IFO-4022 |
| (31) | Streptomyces griseus | IFO-3356 |
| (32) | Gibberella zeae | IFO-7160 |
| (33) | Absidia hyalospora | IFO-8082 |
| (34) | Cunninghamella elegans | IFO-6334 |
| (35) | Gliocladium roseum | IFO-5422 |

In Formula I, when X and Y are both hydrogen and R is $C_1-C_8$ alkoxyl, $C_1-C_8$ alkenyloxy, $C_1-C_8$ alkynyloxy, $C_1-C_4$ halogen-substituted alkyl, $C_1-C_4$ halogen-substituted alkenyl, $C_1-C_4$ halogen-substituted alkynyl, carboxyl, $C_2-C_4$ hydroxycarbonylalkyl which may be substituted with lower alkyl or halogen, or $C_3-C_4$ hydroxycarbonylalkynyl which may be substituted with lower alkyl or halogen, the suitable esterases originate from microorganisms such as (1) through (35) listed by number hereinabove.

All the strains are available from or have been deposited with the Institute Fermentation, Osaka (IFO) or the American Type Culture Collection (ATCC).

Some of the esterases originating from microorganisms have been commercially available in the market. Such commercially available enzymes which can be used are illustrated as follows.

| Name of enzyme | Origin | Selling or manufacturing company |
|---|---|---|
| (36) Lipase AP | Aspergillus sp. | Amano Seiyaku |
| (37) Lipase M-AP | Mucor sp. | Amano Seiyaku |
| (38) Lipase "Amano" P | Pseudomonas sp. | Amano Seiyaku |
| (39) Lipase "Godo" BSL | Arthrobacter ureafaciens nov. var. | Godo Shusei |
| (40) Lipase | genus Arthrobacter | Shinnihon Kagaku |
| (41) Lipase "Toyo" | Chromobacterium viscosum var paralipolytium | Toyo Jozo |
| (42) Lipase "Saiken" | Rhizopus sp. | Osaka Saikin Kenkyusho |
| (43) Lipase AL | Achromobacter sp. | Meito Sangyo |
| (44) Lipase PL No. 266 | Alcaligenes sp. | Meito Sangyo |
| (45) Lipase PL No. 679 | Alcaligenes sp. | Meito Sangyo |

In addition to the foregoing commercially available enzymes listed numerically as (36)–(39), (41)–(45) the following enzymes may also be employed when in Formula I both X and Y are hydrogen:

| Name of enzyme | Origin | Selling or manufacturing company |
|---|---|---|
| (46) Steapsin | Hog pancreas | Tokyo Kasei |

And further when X and Y are both hydrogen in Formula I and R is the residue of a $C_1-C_{18}$ organic carboxylic acid (substituted or unsubstituted), the commercially available enzymes numerically listed hereinabove as (36)–(39), (41), (43)–(46) as well as the following may also be used:

| Name of enzyme | Origin | Selling or manufacturing company |
|---|---|---|
| (47) Pancreatin | Hog pancreas | Tokyo Kasei |
| (48) Esterase | Hog liver | Sigma |

Literature refers to various microorganisms. For example, Lipase Godo BSL (an enzyme originating from *Arthrobactor ureafaciens* nov. var) is described at page 222 of the *Kosoriyo Handbook* published by Chijin Shoin of Tokyo, Japan (1980); Lipase Toyo is described at page 222 of the above-mentioned *Kosoriyo Handbook* (1980) and in a bulletin "Toyo Jozo Enzyme T-01 LIPASE from *Chromobacterium viscosum*" (December 1979) which bulletin refers, inter alia, to Yamaguchi et al. 37 *Agr. Biol. Chem.* 999–1005 (1973); *Alcaligenes* sp. PL-679 (ATCC 31371) (from which Lipase PL-679 is said to be obtained) is reported by the ATCC to be described in U.S. Pat. No. 4,283,494; Lipase PL-266 Meito strain is also said to be described in U.S. Pat. No. 4,283,494; the strain known as Ferm P. No. 1213 (the strain from which Lipase Al is said to be obtained) is described in Japanese Patent publication 49-32080; *Norcardia erythropolis* (IFO 12320) is cross-referenced by the ATCC as (ATCC 21035) and is said to be described in U.S. Pat. Nos. 3,652,395 and in 3,669,836, *Torulopsis candida* (IFO-0380) is cross-referenced by the ATCC as (ATCC-20284) and is said to be described in U.S. Pat. No. 3,733,253; and Achrombacter sp. (ATCC 21910) is said to be described in U.S. Pat. No. 3,871,957.

In carrying out the present invention, the asymmetric hydrolysis of the (R,S)-isomer of the ester represented by the Formula (I) mentioned above is conducted by mixing an esterase-containing liquor, such as a cultured liquor of such microorganism, the filtrate of the cultured liquor, esterase extracted liquor and its concentrate, suspension of microorganism cells or aqueous solution containing treated product thereof such as crude esterase or purified esterase and said (R,S)-isomer of the ester, and stirring or shaking the mixture. Animal pancreas or liver esterase preparations may also be used. If necessary, a non-ester type surfactant may be added. Also it is possible for the enzyme to be in the immobilized form.

The suitable reaction temperature in this reaction is 10° to 65° C., preferably 20° to 50° C. The "(S)-isomer rich" alcohol compound and the resolved (S)-isomer of the alcohol compound may be unstable at a higher temperature. The reaction time usually ranges from 0.5 or 3.0 to 48 hours. The reaction time can be shortened by elevating the reaction temperature or using enzymes having higher activities.

It is important to keep the pH in the reaction at not higher than pH 7, preferably in a range of pH 3.5 to pH 6.0 when Y is F. It is essential to control the pH of the aqueous solution during the asymmetric hydrolysis reaction, because basic substances especially tend to decompose α-cyano-3-phenoxybenzyl alcohol compounds. In a basic medium, the resulting alcohol is subjected to decomposition, though the asymmetric hydrolysis proceeds well by esterase. Accordingly, the hydrolysis reaction should be conducted at not higher than pH 7. Too a low pH tends to cause the deactivation of enzymes. Thus, it is preferred that the reaction is conducted in the range of pH 3.5 to pH 6.3 (when Y is H and X is H). Further, to keep the pH at the level, utilization of a buffer solution is desirable to prevent the lowering of pH value due to the formation of an organic acid, such as acetic acid, during the course of hydrolysis. As the buffer solution, either inorganic or organic acid salt buffer may be employed.

Furthermore, it is preferable to keep the pH constant by utilization of a buffer solution, in order to prevent pH from lowering due to an organic acid such as acetic acid by-produced from the hydrolysis. A buffer solution may be used which contains either an inorganic acid salt or an organic acid salt.

The substrate, the (R,S)-isomer of the ester represented by the Formula I may be used in a concentration of 1 to 80 w/w %, preferably 5 to 35 w/w % or 5 to 40 w/w % on the basis of the reaction mixture.

After carrying out the asymmetric hydrolysis reaction as mentioned above, the optically active α-cyano-benzyl alcohol compound represented by the Formula II in the free form is separated from the unreacted ester of the antipode alcohol compound and they are recovered by an operation such as liquid phase separation by standing, extraction with a solvent or column chromotography to isolate the "(S)-isomer rich" compound or the resolved (S)-isomer. Thus, for example, after the asymmetric hydrolyis reaction, the free (S)-α-cyano-3-phenoxybenzyl alcohol and the unreacted ester of the antipode are separated from the reaction mixture.

Such a separation and recovery operation is conducted, for example, in such a manner that the reaction mixture is extracted with an organic solvent such as ether, benzene or toluene, and the extract is subjected to column chromatography using silica gel, etc. and a cyclohexane-ether (95:5) solution as an eluent to isolate the free optically active α-cyano-benzyl alcohol compound ("(S)-isomer rich" or the resolved (S)-isomer) represented by the Formula (II) and the unreacted antipode ester, respectively or, for example, the extract is subjected to fractionating distillation in vacuo to separate (S)-α-cyano-3-phenoxybenzyl alcohol from the ester of its antipode.

In addition, the unreacted organic carboxylic acid ester which has been separated and recovered as mentioned above is subjected to racemization (e.g. epimerization) by bringing it into contact with a base such as ammonia, pyridine or triethylamine, and can be used again as the starting material.

In Formula I, when X and Y are hydrogen and R is the residue of an organic $C_1$–$C_{18}$ carboxylic acid (substituted or unsubstituted), exemplary organic carboxylic acid moieties ("R") in the esters with (R,S)-α-cyano-3-phenoxybenzyl alcohol are the residues of, for example, formic, acetic, propionic, butyric, valeric, isovaleric, caproic, caprylic, capric, lauric, myristic, palmitic, stearic, oleic, linolic acids, etc. From the viewpoints of ease in handling and optical purity of the reaction product, esters of organic carboxylic acids having 2 to 12 carbon atoms are preferred as the starting material. For handling and economic reasons, the ester of acetic acid is the most preferred. The starting ester may easily be prepared according to the conventional esterification process, for example, by reacting (R,S)-α-cyano-3-phenoxybenzyl alcohol with an anhydride or a halide of such organic carboxylic acid. The ester may also be prepared by reacting 3-phenoxybenzaldehyde and sodium cyanide, with an anhydride or a halide of such organic carboxylic acid.

The (R,S)-isomer of the ester starting material represented by the Formula I (when X is hydrogen, F, Cl or Br and Y is F) can be easily obtained by an ordinary process for producing esters such as, for instance, by a process wherein a halide of an organic carboxylic acid represented by the Formula III:

wherein $R_1$ is a hydrogen atom, a $C_1$–$C_{18}$ alkyl, $C_2$–$C_{18}$ alkenyl, $C_2$–$C_{18}$ alkynyl, $C_1$–$C_4$ halogen-substituted alkyl, $C_2$–$C_4$ halogen-substituted alkenyl, $C_2$–$C_4$ halogen-substituted alkynyl group, for example, acid chloride or acid bromide, or an acid anhydride thereof is allowed to react with an (R,S)-isomer of the α-cyanobenzyl alcohol compound represented by the Formula II (when Y is F), or by a process wherein a halide of the organic carboxylic acid represented by the Formula III mentioned above, for example, acid chloride or acid bromide, an aldehyde compound represented by the Formula IV:

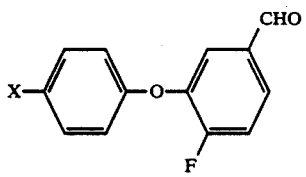

wherein X has the same meaning as above, and sodium cyanide are allowed to react, or by a process wherein one of chloroformic acid esters represented by the Formula V:

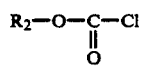

wherein $R_2$ is a $C_1-C_8$ alkyl, $C_2-C_8$ alkenyl or $C_2-C_8$ alkynyl group, is allowed to react with the (R,S)-isomer of α-cyano-benzyl alcohol compound represented by Formula II when Y is F and X is H, F, CR or Br.

Examples of the organic carboxylic acids represented by the Formula III mentioned above are, for instance, formic acid, acetic acid, propionic acid, butyric acid, valeric acid, isovaleric acid, caproic acid, caprylic acid, lauric acid, myristic acid, palmitic acid, stearic acid, oleic acid, linoleic acid, or halogen-substituted compounds thereof and the like. On account of both the ease in handling and the optical purity of the reaction product obtained by the asymmetric hydrolysis, a $C_2-C_{12}$ fatty acid or a $C_1-C_4$ halogen-substituted fatty acid having one chlorine or bromine atom at the α-position thereof is preferable. Further, from the viewpoints of availability and economy, acetic acid, propionic acid, monochloroacetic acid or monobromoacetic acid are more preferred.

Also, in the chloroformic acid ester represented by the Formula V, methyl chlorocarbonate, ethyl chlorocarbonate, propyl chlorocarbonate and the like are preferable from the viewpoints of availability and economy.

Furthermore when Y is F and X is H, F, Cl or Br, the process can be applied to the case wherein the substrate is a half-ester of an organic carboxylic acid of α-cyano-benzyl alcohol compound represented by the Formula II in place of the ester represented by the Formula I.

The starting ester for e.g. Examples 95-128 may easily be prepared according to the conventional esterification process. For example, the carbonic acid ester is prepared by allowing (R,S)-α-cyano-3-phenoxybenzyl alcohol to react with an alkyl chlorocarbonate, e.g., methyl chlorocarbonate, ethyl chlorocarbonate, propyl chlorocarbonate etc. The ester (A) of a halogen substituted organic carboxylic acid is prepared by allowing (R,S)-α-cyano-3-phenoxybenzyl alcohol to react with an anhydride or a halide of such organic acid, preferably, an organic acid having 1 to 2 halogen atoms on the α-position, more preferably, an organic acid having a chlorine or bromine atom on the α-position, such as monochloroacetic acid, monobromoacetic acid etc. Alternatively, the ester (A) may be prepared by reacting 3-phenoxybenzaldehyde and sodium cyanide with a halide of such organic carboxylic acid. The half-ester is prepared by allowing to react (R,S)-α-cyano-3-phenoxybenzyl alcohol with an anhydride of dicarboxylic acid, e.g., oxalic acid, malonic acid, succinic acid, glutaric acid, maleic acid, fumalic acid or its substitution product with lower alkyl group or halogen atom, preferably succinic acid from the view-point of easiness in handling.

EXAMPLES

Examples 1-8

To 15 ml each of an acetate buffer solution having a concentration of 0.2M (pH 4.0) were added 1.0 g each of acetic acid ester of (R,S)-α-cyano-3-phenoxy-4-fluoro-benzyl alcohol and 40 mg each of esterases described in Table 1. The mixtures were allowed to react to 40° C. with stirring. After the reaction was conducted for 24 hours, the reaction mixture each was extracted with toluene. The extract was analyzed with a high-performance liquid chromatography (HPLC) [Lichrosorb RP-18, methanol-water (6:4), 254 nm, UV detection], and the conversion rate was calculated from the peak area ratio of α-cyano-3-phenoxy-4-fluorobenzyl alcohol with acetic acid ester of α-cyano-3-phenoxy-4-fluorobenzyl alcohol.

After concentrating the extract, each concentrate was subjected to a silica gel column chromatography. The elution was conducted with a solution of cyclohexane-ethyl ether (95:5) to separate and remove unaltered acetic acid ester of α-cyano-3-phenoxy-4-fluorobenzyl alcohol. Then, the elutisn was additionally conducted with methanol containing a small amount ($10^{-5}\%$) of p-toluenesulfonic acid until the free α-cyano-3-phenoxyl-4-fluorobenzyl alcohol was obtained.

In 1 ml each of toluene was dissolved 10 mg each of the free α-cyano-3-phenoxy-4-fluorobenzyl alcohol thus obtained. To this solution each was added equimolar chloride of (S)-(+)-2-(4-chlorophenyl)-isovaleric acid together with pyridine. The mixtures were allowed to react to produce (S)-(+)-2-(4-chlorophenyl)-isovaleric diastereomer of α-cyano-3-phenoxy-4-fluorobenzyl alcohol, respectively. The analysis of the optical isomers was conducted with gas chromatography (column: DCQF-1, 2.5 m, column temperature: 250° C.).

The results are shown in Table 1.

TABLE 1

| Example No. | Origin of esterase | Conversion rate (%) | Ratio of optical isomers of free α-cyano-3-phenoxy-4-fluorobenzyl alcohol [(S)-isomer: (R)-isomer] |
|---|---|---|---|
| 1 | genus *Arthrobacter* (Lipase Godo BSL) | 49.6 | 95.8:4.2 |
| 2 | genus *Chromobacterium* (Lipase Godo BSL) | 50.0 | 95.3:4.7 |
| 3 | genus *Pseudomonas* (Lipase "Amano") | 47.9 | 97.5:2.5 |
| 4 | genus *Aspergillus* (Lipase AP) | 44.2 | 79.6:20.4 |
| 5 | genus *Mucor* (Lipase M-AP) | 9.4 | 73.6:26.4 |
| 6 | genus *Alcaligenes* (Lipase PL-679) | 46.2 | 98.1:1.9 |
| 7 | genus *Achromobacter* (Lipase Godo BSL) | 47.2 | 93.8:6.2 |
| 8 | genus *Rhizopus* (Lipase "Saiken") | 13.4 | 80.9:19.1 |

Examples 9-13

To 15 ml each of 0.2M concentration of an acetate buffer solution (pH 4.0) were added 2.0 g each of various esters of (R,S)-isomer of α-cyanobenzyl alcohol mentioned in Table 2, the substrate and 40 mg each of esterases listed in Table 2. The mixtures were allowed to react at 40° C. with stirring. Thereafter the same operation as in Examples 1–8 was conducted. The results are shown in Table 2.

ratio of optical isomers and the conversion rate of the α-cyano-3-phenoxy-4-fluorobenzyl alcohol obtained were measured.

The results are shown in Table 3.

TABLE 2

| Example No. | Origin of esterase | Substrate | Conversion rate (%) | Ratio of optical isomers of free α-cyano-3-phenoxy-benzyl alcohol compounds [(S)-isomer: (R)-isomer] |
|---|---|---|---|---|
| 9 | genus Arthrobacter (Lipase GODO BSL) | Monochloroacetic acid ester of (R,S)-α-cyano-3-(4-chlorophenoxy)-4-fluorobenzyl alcohol | 50.2 | 96.8:3.2 |
| 10 | genus Arthrobacter (Lipase GODO BSL) | Acetic acid ester of (R,S)-α-cyano-3-(4-fluorophenoxy)-4-fluorobenzyl alcohol | 48.9 | 99.3:0.7 |
| 11 | genus Arthrobacter (Lipase GODO BSL) | Acetic acid ester of (R,S)-α-cyano-3 (4-bromophenoxy)-4-fluorobenzyl alcohol | 49.0 | 99.5:0.5 |
| 12 | genus Pseudomonas (Lipase "Amano" P) | Ethyl carbonic acid ester of (R,S)-α-cyano-3-(4-chlorophenoxy)-4-fluorobenzyl alcohol | 47.8 | 97.7:2.3 |
| 13 | genus Chromobacterium (Lipase "Toyo") | Ethyl carbonic acid ester of (R,S)-α-phenoxy)-4-fluorobenzyl alcohol | 43.0 | 96.6:3.4 |
| 14 | genus Arthrobacter (Lipase: Shinnihon Kagaku) | Monochloroacetic acid ester of (R,S)-α-cyano-3-phenoxy-4-fluorobenzyl alcohol | 50.6 | 98.2:1.8 |
| 15 | genus Pseudomonas (Lipase "Amano" P) | Monobromoacetic acid ester of (R,S)-α-cyano-3-phenoxy-4-fluorobenzyl alcohol | 51.5 | 96.5:3.5 |
| 16 | genus Pseudomonas (Lipase: Sinnihon Kagaku) | Ethyl carbonic acid ester of (R,S)-α-cyano-3-phenoxy-4-fluorobenzyl alcohol | 50.0 | 100:0 |

Examples 17–23

In flasks with a shoulder (500 ml each) were charged 100 ml each of a liquid medium, respectively. The medium was a sugared bouillon medium for the bacteria in Examples 17–19, which is prepared by dissolving 10.0 g of glucose, 5.0 g of peptone and 5.0 g of meat extract in 1 liter of water and adjusting the pH to 7.2, or a malt extract-yeast extract medium for the fungi and yeast in Examples 20–23, which is prepared by dissolving 5.0 g of peptone, 10.0 g of glucose, 3.0 g of malt extract and 3.0 g of yeast extract in 1 liter of water and adjusting the pH to pH 6.5. After sterilization, each medium was inoculated with 2 platinum loops of slant cultured microorganisms as described in Table 3 and cultured on a reciprocating shaker at 30° C. for 72 hours.

Then, the pH value of each cultured medium was adjusted to pH 4.5 by using a 2M aqueous solution of hydrochloric acid. 3.0 g of the acetic acid ester of (R,S)-α-cyano-3-phenoxy-4-fluorobenzyl alcohol was added to each cultured medium. The mixtures were allowed to react at 30° C. for 30 hours with stirring, respectively. Thereafter, the separation of the reaction product was conducted in the same manner as in Example 1 and the

TABLE 3

| Example No. | Origin of esterase (cultured microorganisms) | Conversion rate (%) | Ratio of optical isomers of free α-cyano-3-phenoxy-4-fluorobenzyl alcohol [(S)-isomer:(R)-isomer] |
|---|---|---|---|
| 17 | Nocardi erythropolis IFO-12320 | 38.3 | 86.5:13.5 |
| 18 | Bacillus sphaericus IFO-3528 | 21.7 | 62.4:37.6 |
| 19 | Arthrobacter sp. ATCC-21908 | 50.3 | 90.2:9.8 |
| 20 | Rhodotorula Minuta var. texensis IFO-0879 | 47.5 | 82.0:18.0 |
| 21 | Torulopsis candida IFO-0380 | 30.6 | 73.2:26.8 |
| 22 | Candida utilis IFO-1086 | 35.5 | 66.7:33.3 |
| 23 | Hansenula anomala IFO-0707 | 41.3 | 92.1:7.9 |

Examples 24–29

Each of the microorganisms described in Table 4 was cultured in the same process as in Examples 17–23. Then, the pH of each culture medium was adjusted to pH 4.5 by using a 2M aqueous HCl solution. 3.0 g of acetic acid ester of (R,S)-α-cyano-3-(4-chlorophenoxy)-4-fluorobenzyl alcohol was added to each culture medium, and the mixture was allowed to react at 30° C. for 30 hours with stirring. Thereafter, the separation of the reaction product was conducted in the same manner as in Example 1, and the ratio of optical isomers and the conversion rate of the α-cyano-3-(4-chlorophenoxy)-4-fluorobenzyl alcohol obtained were measured.

The results are shown in Table 4.

TABLE 4

| Example No. | Origin of esterase (cultured micro-organisms) | Conversion rate (%) | Ratio of optical isomers of free α-cyano-3-(4-chlorophenoxy)-4-fluorobenzyl alcohol [(S)-isomer:(R)-isomer] |
| --- | --- | --- | --- |
| 24 | Nocardia erythropolis IFO-12320 | 31.8 | 79.7:20.3 |
| 25 | Bacillus sphaericus IFO-3528 | 32.0 | 70.7:29.3 |
| 26 | Rhodotorula minuta var. texensis IFO-0879 | 47.6 | 83.9:16.1 |
| 27 | Torulopsis candida IFO-0380 | 39.8 | 81.0:19.0 |
| 28 | Candida utilis IFO-1086 | 42.3 | 76.6:23.4 |
| 29 | Hansenula anomala IFO-0707 | 48.3 | 69.4:30.6 |

Examples 30 to 33

To 10 ml of 0.2M concentration of an acetate buffer solution (pH 5.0) were added 1.0 g of (R,S)-α-cyano-3-phenoxybenzyl acetate and each 20 mg of an esterase illustrated in Table 5. The mixture was vigorously agitated by means of a magnetic stirrer at 30° C. to advance the reaction. After 24 hours, the reaction mixture was extracted with toluene. The extract was analyzed by high-performance liquid chromatography (HPLC) (Lichrosorb RP-18, MeOH-water (6:4), 254 nm, UV detection), and the conversion was calculated from the peak area ratio of unreacted α-cyano-3-phenoxybenzyl acetate and free α-cyano-3-phenoxybenzyl alcohol. The HPLC analysis also recognized that no 3-phenoxybenzaldehyde had been by-produced during the course of the reaction under the above conditions. The toluene extract was concentrated, and subjected to a silica gel chromatography and eluted with cyclohexane-diethyl ether (94:6) mixture to isolate the unreacted acetate of α-cyano-3-phenoxybenzyl alcohol. The column was then eluted with methanol containing a trace ($10^{-5}$%) of p-toluenesulfonic acid, to obtain free α-cyano-3-phenoxybenzyl alcohol. Its structure was confirmed by HPLC, NMR and IR observations.

Next, the solvent was evaporated away from the elute. Taking a part of the residual alcohol, its specific rotation was measured in chloroform. It was confirmed that the obtained α-cyano-3-phenoxybenzyl alcohol had been the (−)-isomer, i.e. (S)-α-cyano-3-phenoxybenzyl alcohol. (see Table 5).

While, 10 mg of the obtained free α-cyano-3-phenoxybenzyl alcohol was dissolved in 1 ml of tolene, and reacted with an equal mole amount of (S)-(+)-2-(4-chlorophenyl)-isovaleric acid chloride in the presence of pyridine to convert it to a diastereomer of α-cyano-3-phenoxybenzyl (S)-(+)-2-(4-chlorophenyl)-isovalerate, which was analyzed for the optical isomer ratio by gas chromatography (10% DCQF-1, 2.5 m, 250° C.), with the results as shown in the following Table 5.

On the other side, the specific rotation of the unreacted ester recovered from the column after the enzymatic reaction was found to exhibit the negative value in chloroform (for example, $[\alpha]_D = -8.5$ (c=1.5) in Example 30).

TABLE 5

| | | | Free α-cyano-3-phenoxybenzyl alcohol | |
| --- | --- | --- | --- | --- |
| Example No. | Origin of esterase (name of enzyme) | Conversion (%) | Spec. rotation $[\alpha]_D^{25}$, in CHCl$_3$ | Optical isomer ratio (%) [(S)-isomer:(R)-(+)-isomer] |
| 30 | Arthrobacter sp. (Lipase Godo BSL) | 49.8 | −24.5 (c = 1.2) | >99:<1 |
| 31 | Pseudomonas sp. (Lipase "Amano") | 34.0 | −22.2° (c = 1.4) | 93:7 |
| 32 | Aspergillus sp. (Lipase AP) | 47.9 | −16.2 (c = 1.4) | 79:21 |
| 33 | Alcaligenes sp. (Lipase PL No. 266) | 48.9 | −17.2° (c = 0.7) | 82:18 |

Examples 34–39

The same procedures as in Examples 30 to 33 were repeated with the exceptions that the amount of each esterase was 40 mg instead of 20 mg, that the buffer solution was 0.1M concentration of a phosphate buffer solution (pH 6.0) instead of the 0.2M acetate buffer solution (pH 5.0), and that the pH was controlled at the constant level using a pH controller by careful addition of an aqueous 1 M NaOH solution in the form of finely divided water drops using a drop controller. After the enzymatic reaction followed by separation of the reaction product, the resulting (S)-α-cyano-3-phenoxybenzyl alcohol was measured for specific rotation and conversion, with the results as shown in Table 6.

TABLE 6

| Example No. | Origin of esterase (name of enzyme) | Conversion (%) | Free α-cyano-3-phenoxybenzyl alcohol ($[\alpha]_D^{25}$, in CHCl$_3$) |
|---|---|---|---|
| 34 | Arthrobacter sp. (Lipase AL) | 43.7 | −16.0° (c=1.0) |
| 35 | Alcaligenes sp. (Lipase PL No.679) | 52.0 | −17.5° (c=1.2) |
| 36 | Pseudomonas sp. (Lipase "Amano") | 49.7 | −22.5° (c=1.3) |
| 37 | Mucor sp. (Lipase M-AP) | 19.2 | −14.2° (c=0.8) |
| 38 | Hog pancreas (steapsin) | 33.0 | −15.2° (c=0.8) |
| 39 | Hog pancreas (pancreatin) | 30.0 | −15.4° (c=0.8) |

Examples 40 to 48

To 10 ml of 0.2M concentration of an acetate buffer solution (pH 5.4) were added 1.5 g of (R,S)-α-cyano-3-phenoxybenzyl caprate and each 30 mg of an esterase described in Table 7. The mixture was vigorously agitated for 24 hours at 30° C. Thereafter, the separation and analyses were conducted according to the same procedures as in Examples 30 to 33, with the results shown in Table 7.

TABLE 7

| Example No. | Origin of esterase (name of enzyme) | Conversion (%) | Free α-cyano-3-phenoxybenzyl alcohol sp. rotat. ($[\alpha]_D^{25}$, in CHCl$_3$) |
|---|---|---|---|
| 40 | Arthrobacter sp. (Lipase Godo BSL) | 50.1 | −23.0° (c=1.2) |
| 41 | Alcaligenes sp. (Lipase PL No.266) | 49.7 | −19.1° (c=1.0) |
| 42 | Alcaligenes sp. (Lipase PL No.679) | 33.4 | −18.5° (c=1.0) |
| 43 | Achromobacter sp. (Lipase AL) | 27.7 | −17.5° (c=1.0) |
| 44 | Aspergillus sp. (Lipase AP) | 47.8 | −16.3° (c=1.2) |
| 45 | Pseiduomonas sp. (Lipase "Amano") | 39.5 | −22.2° (c=1.2) |
| 46 | Mucor sp. (Lipase M-AP) | 11.2 | −14.1° (c=1.0) |
| 47 | Hog pancreas (steaspsin) | 22.3 | −15.5° (c=0.8) |
| 48 | Hog pancreas (pancreatin) | 17.6 | −14.9° (c=0.8) |

Examples 49 to 54

The same procedures as in Examples 30 to 33 were repeated with the exceptions that the amount of each esterase was 30 mg instead of 20 mg, that the buffer solution was 0.1M concentration of an acetate buffer solution (pH 5.3) instead of the 0.2M acetate buffer solution, that the pH was controlled at the constant level using a pH controller by careful addition of an aqueous 1M NaOH solution in the form of finely divided water drops using a drop controller, and that the amount of the substrate, acetate of (R,S)-α-cyano-3-phenoxybenzyl alcohol, employed was varied from 1.0 g to the values set forth in Table 8. After the enzymatic reaction, followed by separation of the reaction product, the product was measured for conversion, specific rotation and optical isomer ratio by gas chromatography, with the results as shown in Table 8.

TABLE 8

| Example No. | Origin of esterase (name of enzyme) | Amount of substrate (g) | Conversion (%) | Free α-cyano-3-phenoxybenzyl alcohol | |
|---|---|---|---|---|---|
| | | | | spec. rotation ($[\alpha])_D^{25}$[(S)-isomer: in CHCl$_3$) | Optical isomer ratio (R)-(+)-isomer] |
| 49 | Arthobacter sp. (Lipase Godo BSL) | 2.0 | 50.0 | −24.8° (c = 1.2) | 100:0 |
| 50 | Arthrobacter sp. (Lipase Godo BSL) | 3.0 | 49.7 | −23.8° (c = 1.2) | 99:1 |
| 51 | Arthrobacter sp. (Lipase Godo BSL) | 5.0 | 43.6 | −22.0° (c = 1.4) | 93.5:6.5 |
| 52 | Pseudomonas sp. (Lipase "Amano") | 2.5 | 41.1 | −23.2 (c = 1.2) | 99:1 |
| 53 | Alcaligenes sp. (Lipase PL No. 266) | 4.0 | 52.4 | −17.5° (c = 1.3) | 83:17 |
| 54 | Aspergillus sp. (Lipase AP) | 2.0 | 47.4 | −16.4° (c = 1.3) | 78:22 |

Examples 55 to 60

In a 1000 ml Erlenmeyer flask was put 200 ml of a bouillon medium (prepared by dissolving 5.0 g peptone, 5.0 g meat extract and 3.0 g NaCl in 1 liter of water, adding 2 g of tributyrin, in cases of Examples 55 to 57, or 2 g of olive oil, in cases of Examples 58 to 60, and adjusting the pH to 7.2 with Na$_2$HPO$_4$ and KH$_2$PO$_4$) After sterilization, the medium was inoculated with 2 platinum loops of a slant cultured microorganism as illustrated in Table 9, and cultured on a reciprocating shaker at 30° C. for 48 hours. The cultured medium was then contrifuged, and acetone was added to the aqueous solution layer to make 85% concentration. The mixture was immediately filtered, and the separated precipitate was washed with water and dissolved into 15 ml of 0.2M concentration of an acetate buffer solution (pH 5.2). To the solution was added 1.5 g of butyrate, in Examples 55 to 57, or 3.0 g of laurate, in Examples 58 to 60, of (R,S)-α-cyano-3-phenoxybenzyl alcohol. The mixture was vigorously agitated at 33° C. for 26 hours to make the reaction proceed. Thereafter, the separation and analyses were conducted as in Examples 30 to 33, and the conversion and specific rotation were measured with the results as shown in Table 9.

TABLE 9

| Example No. | Origin of esterase (name of microorganism cultured) | Conversion (%) | Free α-cyano-3-phenoxybenzyl alcohol sp. rotat. ($[\alpha]_D^{25}$, in CHCl$_3$) |
|---|---|---|---|
| 55 | Arthrobacter sp. simplex IFO 3530 | 38.7 | −23.0° (c=0.9) |
| 56 | Pseudomonas fragi IFO 3458 | 24.3 | −21.9° (c=0.9) |
| 57 | Alcaligenes faecalis IFO 12669 | 32.3 | −14.2° (c=0.9) |
| 58 | Arthrobacter simplex IFO 3530 | 49.1 | −23.5° (c=1.0) |
| 59 | Pseudomonas fragi IFO 3458 | 39.1 | −22.0° (c=1.0) |
| 60 | Pseudomonas fluorescens IFO 3081 | 32.2 | −18.0° (c=1.0) |

Example 6

To 2 ml of 0.1M concentration of an acetate buffer solution (pH 4.5) were added 8.0 g of (R,S)-α-cyano-3-phenoxybenzyl acetate and 160 mg of esterase from Arthrobacter sp. (Lipase Godo BSL). The mixture was vigorously agitated using an agitation piece at 40° C. to make the reaction proceed. During the reaction, the pH was controlled at the constant level using a pH controller by careful addition of an aqueous 1M NaOH solution in the form of finely divided water drops, using a drop controller. After 24 hours reaction, the reaction product was extracted with toluene.

Thereafter, the same procedures as in Examples 30 to 33 were followed, with the results shown in Table 10.

TABLE 10

| | Free α-cyano-3-phenoxybenzyl alcohol | | |
|---|---|---|---|
| Example No. | Conversion (%) | Specific Rotation ($[\alpha]_D^{25}$, in CHCl$_3$) | Optical isomer ratio (%) [(S)-isomer: (R)-(+)-isomer] |
| 61 | 50.0 | −24.5° (c=1.2) | >99:<1 |

Example 62

To 2 ml of 0.2M concentration of an acetate buffer solution (pH 4.5) were added 8.0 g of (R,S)-α-cyano-3-phenoxybenzyl acetate and 20 mg of esterase from Chromobacterium sp. (Lipase Toyo). The mixture was stirred at 30° C. to make the reaction proceed. During the reaction, the pH was controlled at the constant level using a pH controller by careful addition of an aqueous 1M NaOH solution in the form of finely divided water drops using a drop controller. After 24 hours of reaction, the reaction product was extracted with toluene. Thereafter, the same procedures as in Examples 30 to 33 were followed, with the results shown in Table 11.

TABLE 11

| | | Free α-cyano-3-phenoxybenzyl alcohol | |
|---|---|---|---|
| Example No. | Conversion (%) | Specific Rotation ($[\alpha]_D^{25}$, in CHCl$_3$) | Optical isomer ratio (%) [(S)-isomer: (R)-(+)-isomer] |
| 62 | 47.7 | −23.5° (c=1.0) | 98.0:2 |

Examples 63 to 92

100 ml of liquid medium [a sugared bouillon medium (prepared by dissolving 10.0 g of glucose, 5.0 g of peptone, 5.0 g of meat extract and 3.0 g of NaCl in 1 liter of water and adjusting to pH 7.2) for bacteria as in Examples 63 to 66 and 71 to 78, or a malt extract-yeast extract medium (prepared by dissolving 5.0 g of peptone, 10.0 g of glucose, 3.0 g of malt extract and 3.0 g of yeast extract in 1 liter of water, and adjusting to pH 7.2) for fungi and yeasts as in Examples 67 to 70 and 79 to 92] was put in a 500 ml flask having a shoulder. After sterilization, the medium, was inoculated with 2 platium loops of a slant cultured microorganism as illustrated in Table 8, and cultured on a reciprocating shaker at 30° C. for 72 hours. The pH value of the cultured medium was adjusted to pH 5.0 by use of an aqueous 2M HCl solution. 2.0 g of (R,S)-α-cyano-3-phenoxybenzyl acetate was added to the cultured medium, and the mixture was agitated at 30° C. for 30 hours to make the reaction proceed. During the reaction, the pH was controlled at the constant level in a way similar to Example 62.

Thereafter, the reaction product was separated as in Examples 30 to 33, and the obtained α-cyano-3-phenoxybenzyl alcohol was measured for the opticalisomer ratio and conversion, with the results shown in Table 12.

TABLE 12

| Example No. | Origin of esterase (microorganism cultured) | Conversion (%) | Free α-cyano-3-phenoxybenzyl alcohol, optical isomer ratio (S)-isomer:(R)-(+)-isomer |
|---|---|---|---|
| 63 | Bacillus cereus (ATCC-13366) | 50.3 | 87.3:12.7 |
| 64 | Bacillus licheniformis (IFO-12197) | 18.5 | 96.0:4.0 |
| 65 | Macrococcus luteus (IFO-3066) | 25.9 | 79.5:20.5 |
| 66 | Nocardia erythropolis (IFO-12320) | 39.2 | 88.4:11.6 |
| 67 | Rhodotorula minuta (IFO-0387) | 47.1 | 89.1:10.9 |
| 68 | Rhodotorula minuta var. texensis (IFO-0879) | 49.6 | 96.5:3.5 |
| 69 | Torulopsis candida (IFO-0380) | 17.0 | 88.3:11.7 |
| 70 | Candida utilis (IFO-1086) | 19.0 | 75.4:24.6 |

TABLE 12-continued

| Example No. | Origin of esterase (microorganism cultured) | Conversion (%) | Free α-cyano-3-phenoxybenzyl alcohol, optical isomer ratio (S)-isomer:(R)-(+)-isomer |
|---|---|---|---|
| 71 | *Chromobacterium violaceum* (IFO-12614) | 27.4 | 90.5:9.5 |
| 72 | *Brevibacterium ammoniagenes* (IFO-12072) | 43.9 | 89.2:10.8 |
| 73 | *Enterobacter cloacae* (IFO-3320) | 23.1 | 85.7:14.3 |
| 74 | *Flavobacterium arborescens* (IFO-3750) | 26.5 | 64.6:45.4 |
| 75 | *Mycobacterium phlei* (IFO-3158) | 31.7 | 77.3:22.7 |
| 76 | *Corynebacterium equi* (ATCC-7699) | 34.3 | 72.3:27.6 |
| 77 | *Lactobacillus casei* (IFO-3322) | 13.9 | 76.1:23.9 |
| 78 | *Streptomyces griseus* (IFO-3356) | 25.7 | 77.5:22.5 |
| 79 | *Trichoderma viride* (IFO-4847) | 48.0 | 81.9:18.1 |
| 80 | *Penicillium freguentans* (IFO-5692) | 30.0 | 82.7:17.3 |
| 81 | *Rhizopus chinensis* (IFO-4737) | 39.7 | 89.0:11.0 |
| 82 | *Aureobasidium pullulans* (IFO-4464) | 26.2 | 80.1:19.9 |
| 83 | *Actinomucor elegans* (IFO-4022) | 37.5 | 88.2:11.8 |
| 84 | *Gibberella zeae* (IFO-7160) | 11.8 | 85.5:17.0 |
| 85 | *Geotrichum candidum* (IFO-5368) | 35.8 | 83.0:17.0 |
| 86 | *Absidia hyalospora* (IFO-8082) | 10.7 | 77.4:22.6 |
| 87 | *Cunninghamella elegans* (IFO-6334) | 25.9 | 79.7:20.3 |
| 88 | *Gliocladium roseum* (IFO-5422) | 8.9 | 83.1:16.9 |
| 89 | *Saccharomyces rouxii* (IFO-0505) | 17.5 | 67.8:32.2 |
| 90 | *Cryptococcus albidus* (IFO-0378) | 13.6 | 69.1:30.9 |
| 91 | *Pichia polymorpha* (IFO-1166) | 32.8 | 75.7:24.3 |
| 92 | *Hansenula anomala* (IFO-0707) | 40.1 | 77.4:22.6 |

Example 93

One liter of a cultured medium of *Rhodotorula minuta* var. texensis (IFO-0879) prepared in the same way as in Example 68 was centrifuged. The collected cells were washed twice with distilled water and then freeze-dried. To 10 ml of 0.2M concentration of an acetate buffer solution (pH 5.0) were dissolved 500 mg of the freeze-dried cells and 3.0 g of (R,S)-α-cyano-3-phenoxybenzyl butyrate. The mixture was agitated at 40° C. for 20 hours to advance the reaction. Thereafter, the separation and analysis were conducted according to the procedures similar to those in Examples 30 to 33. The resulting free α-cyano-3-phenoxybenzyl alcohol was measured for conversion and optical isomer ratio, with the results shown in Table 13.

TABLE 13

| Example No. | Conversion (%) | Free α-cyano-3-phenoxybenzyl alcohol, optical isomer ratio [(S)-isomer:(R)-(+)-isomer] |
|---|---|---|
| 93 | 50.0 | 98.3:1.7 |

Example 94

Into a 2 liter jar fermenter was placed 1 liter of an olive oil-added bouillon medium (prepared by dissolving 5.0 g of peptone, 5.0 g of meat extract and 3.0 g of NaCl in 1 liter of water, adding 2.0 g of olive oil thereto, land adjusting to pH 7.0). After sterilization, the medium was inoculated with *Bacillus cereus* (ATCC-13366), and cultured under aeration-agitation at 30° C. for 72 hours. Then, the medium was centrifuged, and the aqueous layer was concentrated to 3 times concentration. Acetone was added to the concentrate to make the 85% concentration. The mixture was immediately filtered, and the obtained precipitate was washed with water and dissolved into 10 ml of 0.2M concentration of an acetate buffer solution (pH 4.5). 5.0 g of (R,S)-α-cyano-3-phenoxybenzyl laurylate was added to the solution, and the mixture was vigorously agitated for 16 hours at 40° C. to advance the reaction. Thereafter, the separation and analyses were conducted according to the procedures similar to those in Examples 30 to 33. Conversion and optical isomer ratio of free α-cyano-3-phenoxybenzyl alcohol were measured, with the results shown in Table 14.

TABLE 14

| Example No. | Conversion (%) | Free α-cyano-3-phenoxybenzyl alcohol, optical isomer ratio [(S)-isomer:(R)-(+)-isomer] |
|---|---|---|
| 94 | 46.6 | 96.9:3.1 |

Examples 95 to 102

To 15 ml of 0.2M concentration of an acetate buffer solution (pH 4.0) were added 2.0 g of (R,S)-α-cyano-3-phenoxybenzyl ethylcarbonate and each 40 mg of an esterase illustrated in Table 1. The mixture was stirred at 40° C. for 24 hours. And then, the reaction mixture was extracted with toluene. The extract was analyzed by high-performance liquid chromatography (HPLC) (Lichrosorb RP-18, MeOH-water (6:4), 254 nm, UV detection), and the rate of the hydrolysis was calculated from the peak area ratio of unreacted α-cyano-3-phenoxybenzyl ethylcarbonate and free α-cyano-3-phenoxybenzyl alcohol. The toluene extract was concentrated, and subjected to a silica gel chromatography and eluted with cyclohexane-diethyl ether (95:5) mixture to isolate the unaltered ethylcarbonate of α-cyano-3-phenoxybenzyl alcohol, followed by being removed. The column was then eluted with methanol containing a trace ($10^{-5}$%) of p-toluenesulfonic acid, to obtain the solution of free α-cyano-3-phenoxybenzyl alcohol.

After removing the solvent from the elute, 10 mg of the obtained free α-cyano-3-phenoxybenzyl alcohol was dissolved in 1 ml of toluene, and reacted with an equal mole amount of (S)-(+)-2-(4-chlorophenyl)-isovaleric acid chloride in the presence of pyridine to convert it to a diastereomer of α-cyano-3-phenoxybenzyl (S)-(+)-2-(4-chlorophenyl)-isovalerate, which was analyzed for the optical isomer ratio by gas chromatography (10% DCQF-1, 2.5 m, 250° C.).

The results are shown in Table 15.

Examples 103 to 108

100 ml of liquid medium [a sugared bouillon medium (prepared by dissolving 10.0 g of glucose, 5.0 g of peptone, 5.0 g of meat extract and 3.0 g of Nacl in 1 liter of water and adjusting to pH 7.2) for bacteria as in Examples 103 and 104, or a malt extract-yeast extract medium (prepared by dissolving 5.0 g of peptone, 10.0 g of glucose, 3.0 g of malt extract and 3.0 g of yeast extract in 1 liter of water, and adjusting to pH 6.5) for the fungi and yeasts as in Examples 105 to 108] was placed into a 500 ml flask having a shoulder. After sterilization, the medium was inoculated with 2 platinum loops of a slant cultured microorganism as illustrated in Table 16, and cultured on a reciprocating shaker at 30° C. for 72 hours. The pH value of the cultured medium was adjusted to pH 4.5 by use of an aqueous 2M HCl solution. 3.0 g of (R,S)-α-cyano-3-phenoxybenzyl propylcarbonate was added to the cultured medium and the mixture was stirred at 30° C. for 30 hours.

Thereafter, the rate of the hydrolysis and the optical isomer ratio of the free α-cyano-3-phenoxybenzyl alcohol obtained was calculated by using same procedures as in Examples 95 to 102.

The results are shown in Table 16.

TABLE 16

| Example No. | Origin of esterase (name of enzyme) | Rate of hydrolysis (%) | Optical isomer ratio of free α-cyano-3-phenoxybenzyl) alcohol [(S)-isomer:(R)-isomer] |
|---|---|---|---|
| 103 | Norcardia erythropolis IFO-12320 | 13.0 | 85.2:14.8 |
| 104 | Bacillus sphaericus IFO-3528 | 13.0 | 61.5:38.5 |
| 105 | Rhotorula minuta var. texensis | 31.8 | 73.0:27.0 |
| 106 | Torulopsis candida IFO-0380 | 21.3 | 75.8:4.2 |
| 107 | Candida utilis IFO-1086 | 22.6 | 60.3:39.7 |
| 108 | Hansenula anomala IFO-0707 | 33.7 | 90.9:9.1 |

Example 109 to 117

To 15 ml to 0.2M concentration of acetate buffer solution (pH 4.0) were added 4.0 g of (R,S)-α-cyano-3-phenoxybenzyl monochloroacetate and 40 mg of an esterase illustrated in Table 17. The mixture was stirred at 40° C. for 5 hours while controlling the pH value at

TABLE 15

| Example No. | Origin of esterase (name of enzyme) | Ratio of hydrolysis (%) | Optical isomer ratio of free α-cyano-3-phenoxybenzyl alcohol [(S)-isomer:(R)-isomer] |
|---|---|---|---|
| 95 | Arthrobacter ureafaciens nor. var. (Lipase Godo BSL) | 52.1 | 93.7:6.3 |
| 96 | Chromobacterium sp. (Lipase "Toyo") | 50.0 | 100:0 |
| 97 | Pseudomonas sp. (Lipase "Amano" P) | 10.2 | 89.3:10.7 |
| 98 | Aspergillus sp. (Lipase AP) | 14.9 | 83.3:16.7 |
| 99 | Mucor sp. (Lipase M-AP) | 9.5 | 62.4:37.6 |
| 100 | Alcaligenes sp. (Lipase PL-679) | 37.2 | 85.1:14.9 |
| 101 | Achromobacter sp. (Lipase AL) | 46.6 | 79.5:20.5 |
| 102 | Rhizopus sp. (Lipase "Saiken") | 6.3 | 94.1:5.9 | a constant level (using a pH controller) by addition of an aqueous 1M NaOH solution in the form of finely divided water drops formed by a drop controller. Thereafter, the rate of the hydrolysis and the optical isomer ratio of the obtained free α-cyano-3-phenoxybenzyl alcohol were caculated by the same procedures as in Examples 95 to 102. The results are shown in Table 17.

phenoxybenzyl acid succinate and 50 mg of an esterase illustrated in Table 19. The mixture was stirred at 40° C. for 24 hours while maintaining the pH value at a constant level in the same procedures as in Examples 109 to 117. Thereafter, the rate of hydrolysis was calculated by the similar way to Examples 95 to 102. Then the toluene extract was concentrated and subjected to a silica gel chromatography and eluted with cyclohexane-diethyl ether (92:8) mixture to isolate the unaltered acid succinate of an α-cyano-3-phenoxybenzyl alcohol. Thereafter, free α-cyano-3-phenoxybenzyl alcohol alcohol was obtained and analyzed by the same procedures as in Examples 95 to 102. The results are shown in Table 19.

TABLE 17

| Example No. | Origin of esterase (name of enzyme) | Ratio of hydrolysis (%) | Optical isomer ratio of free α-cyano-3-phenoxybenzyl alcohol [(S)-isomer:(R)-isomer |
|---|---|---|---|
| 109 | Arthrobacter ureafaciens nov. var. (Lipase Godo BSL) | 53.9 | 93.0:7.0 |
| 110 | Chromobacterium sp. (Lipase "Toyo") | 50.0 | 100:0 |
| 111 | Pseudomonas sp. (Lipase "Amano") | 49.5 | 93.9:6.1 |
| 112 | Aspergillus sp. (Lipase AP) | 70.3 | 63.4:36.6 |
| 113 | Mucor sp. (Lipase MAP) | 28.3 | 83.8:16.2 |
| 114 | Alcaligenes sp. (Lipase PL-679) | 49.0 | 70.3:29.7 |
| 115 | Achromobacter sp. (Lipase AL) | 45.7 | 88.1:11.9 |
| 116 | Rhizopus sp. (Lipase "Saiken") | 24.6 | 89.9:10.1 |
| 117 | Hog pancreas (steapsin) | 35.1 | 79.4:20.6 |

Examples 118 to 122

100 ml of a malt extract-yeast extract medium (which was prepared by the same procedures as in Examples 105 to 108) was put into a 500 ml flask having a shoulder. After sterilization, the medium was inoculated with 2 platinum loops of a slant cultured microorganism as illustrated in Table 18, and cultured on a reciprocating shaker at 30° C. for 72 hours. The pH value of the cultured medium was adjusted to pH 4.5 by use of an aqueous 2M HCl solution. 2.0 g of (R,S)-α-cyano-3-phenoxybenzyl monobromoacetate was added to the cultured medium, and the mixture was stirred at 30° C. for 15 hours while maintaining the pH value at a constant level in a way similar to Examples 109 to 117.

Thereafter, the rate of the hydrolysis and the optical isomer ratio of the obtained free α-cyano-3-phenoxybenzyl alcohol were calculated by the same procedures as in Examples 95 to 102. The results are as shown in Table 18.

TABLE 18

| Example No. | Origin of esterase (name of enzyme) | Ratio of hydrolysis (%) | Optical isomer ratio of free α-cyano-3-phenoxybenzyl alcohol [(S)-isomer:(R)-isomer] |
|---|---|---|---|
| 118 | Rhodotorula minuta var. texensis IFO-0879 | 39.5 | 64.5:34.5 |
| 119 | torulopsis candida IFO-0380 | 28.1 | 65.2:34.8 |
| 110 | Candida utilis IFO-1086 | 38.5 | 61.2:38.8 |
| 111 | Hansenula anomala IFO-0707 | 44.0 | 63.3:36.7 |
| 113 | Trichoderma viride IFO-4847 | 31.0 | 70.1:29.9 |

TABLE 19

| Example No. | Origin of esterase (name of enzyme) | Ratio of hydrolysis (%) | Optical isomer ratio of free α-cyano-3-phenoxybenzyl) alcohol [(S) isomer:(R)-isomer] |
|---|---|---|---|
| 123 | Chromobacterium viscosum (Lipase "Toyo") | 39.4 | 78.2:21.8 |
| 124 | Arthrobacter ureafaciens nov. var. (Lipase Godo BSL) | 20.7 | 62.5:37.5 |

Examples 123 to 124

To 20 ml of 0.2M concentration of acetate buffer solution (pH 4.0) were added 2.5 g of (R,S)-α-cyano-3-

Examples 125 to 128

The cultured medium of a microorganism illustrated in Table 20 was prepared by the same procedures as in Examples 118 to 122. To the cultured medium was added 2.0 g of sodium (R,S)-α-cyano-3-phenoxybenzyl succinate and the mixture was stirred at 35° C. for 30 hours while maintaining the pH value at a constant level in the same procedures as in Examples 109 to 117. Thereafter, the rate of hydrolysis and the optical isomer ratio of obtained free α-cyano-3-phenoxybenzyl alcohol were calculated in the similar way to Examples 123 to 124. The results are shown in Table 20.

TABLE 20

| Example No. | Origin of esterase (microosganism cultured) | Ratio of hydrolysis (%) | Optical isomer ratio of free α-cyano-3-phenoxybenzyl [(S)-isomer: (R)-isomer] |
| --- | --- | --- | --- |
| 125 | Rhodotorula minuta var. texensis IFO-0879 | 23.8 | 62.3:37.7 |
| 126 | Torulopsis candida IFO-0380 | 11.3 | 77.1:23.9 |
| 127 | Hansenula anomala IFO 0707 | 11.4 | 82.6:17.4 |
| 128 | Candida utilis IFO-1086 | 11.3 | 58.2:41.8 |

What is claimed is:

1. The process for producing an (S)-isomer rich optically active α-cyano-benzyl alcohol compound represented by the Formula (II):

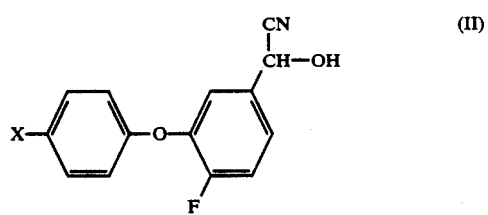

wherein X is a hydrogen atom, fluorine atom, chlorine atom or bromine atom, which process comprises asymmetrically hydrolyzing an ester of (R,S)-isomer of α-cyano-benzyl alcohol compound represented by the Formula I:

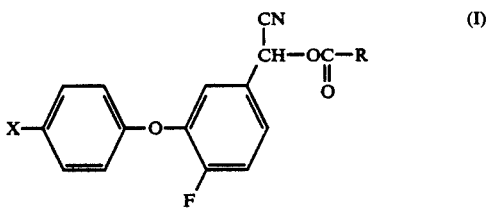

wherein X has the same meaning as above; R means a hydrogen atom, a $C_1$–$C_{18}$ alkyl, $C_2$–$C_{18}$ alkenyl, $C_2$–$C_{18}$ alkynyl, $C_1$–$C_4$ halogen substituted alkyl, $C_2$–$C_4$ halogen-substituted alkenyl, $C_1$–$C_8$ alkoxyl, $C_2$–$C_8$ alkenyloxy or $C_2$–$C_8$ alkynyloxy, with an esterase orginating from microorganisms belonging to genus Arthrobacter, genus Alcalingenes, genus Achromobacter, genus Pseudomonas or genus Chromobacterium under conditions sufficient to convert the (R,S) isomer to an optically active mixture containing 73.2% or more of the (S)-isomer.

2. The process according to claim 1, wherein, in the ester of the (R,S)-isomer of α-cyano benzyl alcohol compounnd represented by the formula (I), the R group is a $C_1$–$C_{11}$ alkyl group, $C_2$–$C_{11}$ alkenyl group, $C_2$–$C_{11}$ alkynyl group, $C_1$–$C_4$ alkyl group having a chlorine atom or bromine atom at the α-position thereof, $C_2$–$C_4$ alkenyl group having a chlorine atom or bromine atom at the α-position thereof, $C_2$–$C_4$ alkynyl group having a chlorine atom or bromine atom at the α-position thereof, or $C_1$–$C_3$ alkoxyl group.

3. The process according to claim 2, wherein, in the ester of the (R,S)-isomer of the α-cyano-benzyl alcohol compound represented by the formula (I), the R group is methyl, ethyl, monochloromethyl, monobromomethyl, methoxy, ethoxy or propoxy.

4. The process according to claim 1, wherein the asymmetric hydrolysis reaction is conducted in a pH range of 3.5 to 6.0.

5. The process according to claim 1, wherein the asymmetric hydrolysis reaction is conducted at 20°–50° C.

6. The process according to claim 3, wherein the asymmetric hydrolysis reaction is conducted at 20°–50° C. in a pH range of 3.5 to 6.0.

7. The process according to claim 2, wherein the asymmetric hydrolysis reaction is conducted at 20°–50° C. in a pH range of 3.5 to 6.0.

8. The process for producing an optically active α-cyano-benzyl alcohol compound represented by the Formula (II):

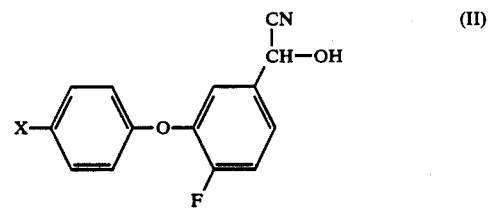

wherein X is a hydrogen atom, fluorine atom, chlorine atom or bromine atom, which process comprises asymmetrically hydrolyzing an ester of the (R,S)-isomer of the α-cyano-benzyl alcohol compound represented by the Formula (I):

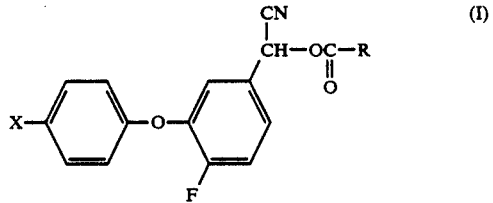

wherein X has the same meaning as above; R means a hydrogen atom, a $C_1$-$C_{18}$ alkyl, $C_2$-$C_{18}$ alkenyl, $C_2$-$C_{18}$ alkynyl, $C_1$-$C_4$ halogen-substituted alkyl, $C_2$-$C_4$ halogen-substituted alkenyl, $C_2$-$C_4$ halogen-substituted alkynyl, $C_1$-$C_8$ alkoxyl, $C_2$-$C_8$ alkenyloxy or $C_2$-$C_8$ alkynyloxy group, with an esterase orginating from *Hansenula anomala* (IFO-0707), *Arthrobacter* sp. (ATCC-21908), *Rhodotorula minuta* var. texensis (IFO-0879), *Norcardia erythropolis* (IFO-12320) or *Torulopsis candida* (IFO-0380) under conditions sufficient to convert the (R,S)-isomer to an optically active mixture containing 73.2% or more of the (S)-isomer.

9. The process according to claim 8, wherein, in the ester of (R,S)-isomer of α-cyano-benzyl alcohol compound represented by the formula (I), the R group is a $C_1$-$C_{11}$ alkyl group, $C_2$-$C_{11}$ alkenyl group, $C_2$-$C_{11}$ alkynyl group, $C_1$-$C_4$ alkyl group having a chlorine atom or bromine atom at the α-position thereof, $C_2$-$C_4$ alkenyl group having a chlorine atom or bromine atom at the α-position thereof, $C_2$-$C_4$ alkynyl group having a chlorine atom or bromine atom at the α-position thereof, or $C_1$-$C_3$ alkoxyl group.

10. The process according to claim 9, wherein, in the ester of the (R,S)-isomer of the α-cyano-benzyl alcohol compound represented by the formula (I), the R group is methyl, ethyl, monochloromethyl, monobromomethyl, methoxy, ethoxy or propoxy.

11. The process according to claim 8, wherein the asymmetric hydrolysis reaction is conducted in a pH range of 3.5 to 6.0.

12. The process according to claim 8, wherein the asymmetric hydrolysis reaction is conducted at 20°-50° C.

13. The process according to claim 9, where the asymmetric hydrolysis reaction is conducted at a temperature of 20°-50° C. and in a range of pH of 3.5 to 6.0.

14. The process according to claim 10, wherein the asymmetric hydrolyis reaction is conducted at temperature of 20°-50° C. and in a pH range of 3.5 to 6.0.

15. The process for producing an optionally active α-cyano-benzyl alcohol compound represented by the formula (II):

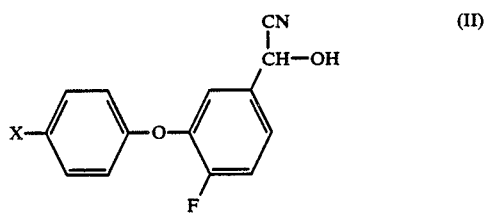

(II)

wherein X is a hydrogen atom, fluorine atom, chlorine atom or bromine atom, which process comprises asymmetrically hydrolyzing an ester of (R,S)-isomer of cyano-benzyl alcohol compound represented by the formula (I):

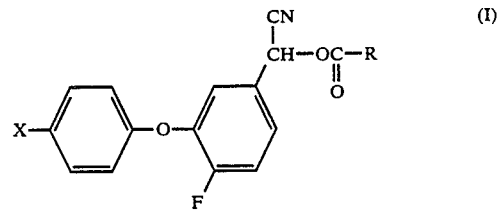

(I)

wherein X has the same meaning as above; R means a hydrogen atom, a $C_1$-$C_{18}$ alkyl, $C_2$-$C_{18}$ alkenyl, $C_2$-$C_{18}$ alkynyl, $C_1$-$C_4$ halogen-substituted alkyl, $C_2$-$C_4$ halogen-substituted alkenyl, $C_2$-$C_4$ halogen-substituted alkynyl, $C_1$-$C_8$ alkoxyl, $C_2$-$C_8$ alkenyloxy or $C_2$-$C_8$ alkynyloxy group, with an esterase originating from microorganisms belonging to genus Arthrobacter, genus Alcalingenes, genus Achromobacter, genus Pseudomonas, genus Chromobacterium, genus Nocardia, genus Rhodotorula, genus Rhizopus, or genus Torulopsis under conditions sufficient to convert the (R,S)-isomer to an optically active mixture containing approximately 73.2% or more of the (S)-isomer.

16. The process according to claim 15, wherein, in the ester of the (R,S)-isomer of α-cyano-benzyl alcohol compound represented by the formula (I), the R group is a $C_1$-$C_{11}$ alkyl group, $C_2$-$C_{11}$ alkenyl group, $C_2$-$C_{11}$ alkynyl group $C_1$-$C_4$ alkyl group having a chlorine atom or bromine atom at the α-position thereof, $C_2$-$C_4$ alkenyl group having a chlorine atom or bromine atom at the α-position thereof, $C_2$-$C_4$ alkynyl group having a chlorine atom or bromine atom at the α-position thereof, or $C_1$-$C_3$ alkoxyl group.

17. The process according to claim 16, wherein, in the ester of the (R,S)-isomer of the α-cyano-benzyl alcohol compound represented by the formula (I), the R group is methyl, ethyl, monochloromethyl, monobromomethyl, methoxy, ethoxy or propoxy.

18. The process according to claim 15, wherein the asymmetric hydrolysis reaction is conducted in a pH range of 3.5 to 6.0.

19. The process according to claim 15, wherein the asymmetric hydrolysis reaction is conducted at 20°-50° C.

20. The process according to claim 16, wherein the asymmetric hydrolysis reaction is conducted at 20°-50° C. in a pH range of 3.5 to 6.0.

21. The process according to claim 17, wherein the asymmetric hydoloysis reaction is conducted at 20°-50° C. in a pH range of 3.5 to 6.0.

22. The method for preparing optically active α-cyano-3-phenoxybenzyl alcohol which comprises reacting a racemic mixture of an organic carboxylic acid ester of (R,S)-α-cyano-3-phenoxybenzyl alcohol, said organic acid being a $C_1$-$C_{18}$ saturated or unsaturated carboxylic acid with an esterase isloated from a microorganism selected from the group consisting of *Chromobacterium violaceum*, *Arthrobacter ureafaciens* nov. var., *Bacillus cereus*, *Bacillus licheniformis* and *Rhodotorula minuta* var. texensis, under conditions sufficient to convert said racemic mixture to an optically active mixture containing approximately 90% or more of the (S)-(—)-α-cyano-3-phenoxybenzyl alcohol and recovering the optically active fraction thus produced.

* * * * *